United States Patent [19]

Pitteloud

[11] Patent Number: 5,654,430

[45] Date of Patent: Aug. 5, 1997

[54] OLIGOMERIC ALIPHATIC HALS PHOSPHITES AND HALS PHOSPHONITES AS STABILIZERS

[75] Inventor: Rita Pitteloud, Praroman, Switzerland

[73] Assignee: Ciba-Geigy Corporation, Tarrytown, N.Y.

[21] Appl. No.: 416,655

[22] Filed: Apr. 5, 1995

[30] Foreign Application Priority Data

Apr. 13, 1994 [CH] Switzerland ............... 1114/94

[51] Int. Cl.$^6$ .................................................. C07D 211/46
[52] U.S. Cl. .................. 546/24; 546/25; 524/102; 528/400
[58] Field of Search .................. 546/24, 25; 524/102; 528/400

[56] References Cited

U.S. PATENT DOCUMENTS

| | | | |
|---|---|---|---|
| 4,233,412 | 11/1980 | Rody et al. | 525/167 |
| 4,325,863 | 4/1982 | Hinsken et al. | 624/111 |
| 4,338,244 | 7/1982 | Hinsken et al. | 524/109 |
| 5,175,312 | 12/1992 | Dubs et al. | 549/307 |
| 5,216,052 | 6/1993 | Nesvadba et al. | 524/108 |
| 5,239,076 | 8/1993 | Meier et al. | 546/187 |
| 5,252,643 | 10/1993 | Nesvadba | 524/111 |
| 5,356,966 | 10/1994 | Nesvadba | 524/111 |
| 5,405,891 | 4/1995 | Pitteloud | 524/102 |

FOREIGN PATENT DOCUMENTS

| | | |
|---|---|---|
| 2106608 | 3/1994 | Canada . |
| 356688 | 3/1990 | European Pat. Off. . |
| 487036 | 5/1992 | European Pat. Off. . |
| 589839 | 3/1994 | European Pat. Off. . |
| 591102 | 4/1994 | European Pat. Off. . |
| 0601973 | 6/1994 | European Pat. Off. . |
| 2380290 | 9/1978 | France . |
| 3928291 | 2/1991 | Germany . |
| 4306747 | 9/1993 | Germany . |
| 4316611 | 11/1993 | Germany . |
| 4316622 | 11/1993 | Germany . |
| 4316876 | 11/1993 | Germany . |
| 2247241 | 2/1992 | United Kingdom . |
| 2265377 | 9/1993 | United Kingdom . |

OTHER PUBLICATIONS

R. Gächter/H. Müller, Plastics Additives Handbook 3rd Ed. p. 47 1990, Hanser, München.
T. König et al. J. Prakt. Chem. vol. 334, pp. 333–349 (1992).
R. Bartlett et al. J. Amer. Chem. Soc. vol. 109 (19), 5699 (1987).
Organic Synthesis, Coll. vol. IV, 784 (1963).
Th. Veil et al., Helv. Chim. Acta 1952, 1412.
F. Nief et al Tetrahedron vol. 47 (33) 6673 (1991).
Ullmanns Encyklopädie der Technischen Chemie BD, 13, Seiten 85–94 (1977).
Derw. Abst. 93–296322 of DE 4,306,747 (1993).
Derw. Abst. 91–066407 of DE 3,928,291 (1991).

*Primary Examiner*—C. Warren Ivy
*Assistant Examiner*—Garth M. Dahlen
*Attorney, Agent, or Firm*—Michele A. Kovaleski; Luther A. R. Hall

[57] ABSTRACT

The invention relates to novel oligomeric compounds of the formula I

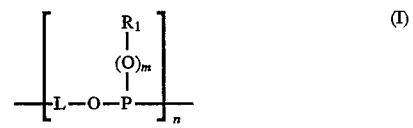

in which L is a group of the formula

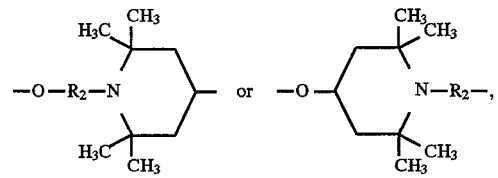

where the oxygen in the group L is in each case bonded to the phosphorus in the recurring structural units and the radical $R_2$ or the carbon in the 4-position of the piperidinyl ring in the group L is in each case bonded to the oxygen in the recurring structural units; and the general symbols are as defined in claim 1, as stabilizers for organic materials against oxidative, thermal or light-induced degradation.

27 Claims, No Drawings

OLIGOMERIC ALIPHATIC HALS PHOSPHITES AND HALS PHOSPHONITES AS STABILIZERS

The present invention relates to novel oligomeric aliphatic HALS phosphites and HALS phosphonites, to compositions comprising an organic material, preferably a polymer, and the novel oligomeric aliphatic HALS phosphites and HALS phosphonites, and to the use thereof for the stabilization of organic materials against oxidative, thermal or light-induced degradation.

Organic phosphites and phosphonites are known in industry as costabilizers, secondary antioxidants and processing stabilizers, inter alia for polyolefins; examples of such known phosphite stabilizers are given in R. G ächter/H. Müller (Eds.), Plastics Additives Handbook, 3rd Ed., p. 47, Hanser, Munich, 1990, and EP-A-356 688.

Hindered amines, including, in particular, compounds containing 2,2,6,6-tetramethylpiperidyl groups, are preferably used as light stabilizers (hindered amine light stabilizers, HALS).

Phosphites and phosphonites containing HALS structural units are described, for example, by T. König et al, J. prakt. Chem. 334, 333–349 (1992), in U.S. Pat. No. 5,239,076, GB-A-2 247 241, DE-A-4 306 747 and FR-A-2 380 290.

There continues to be a demand for effective stabilizers for organic materials which are sensitive to oxidative, thermal and/or light-induced degradation.

It has now been found that a selected group of such HALS phosphites and HALS phosphonites is particularly suitable as stabilizers for organic materials which are sensitive to oxidative, thermal or light-induced degradation. Particular mention should be made of the suitability of said compounds as processing stabilizers for synthetic polymers.

The present invention therefore relates to oligomeric compounds of the formula I

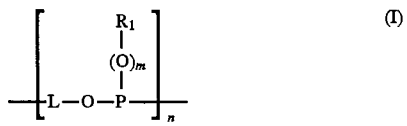

in which L is a group of the formula

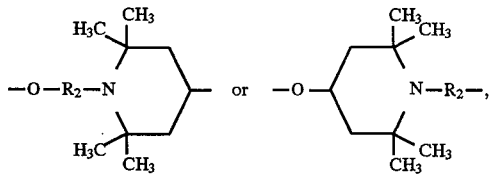

where the oxygen in the group L is in each case bonded to the phosphorus in the recurring structural unit and the radical $R_2$ or the carbon in the 4-position of the piperidinyl ring in the group L is in each case bonded to the oxygen in the recurring structural unit;

$R_1$ is $C_1$–$C_{25}$alkyl, $C_2$–$C_{25}$alkyl which is interrupted by oxygen, sulfur or >N—$R_3$; $C_2$–$C_{24}$alkenyl, unsubstituted or $C_1$–$C_4$alkyl-substituted $C_5$–$C_{15}$cycloalkyl; unsubstituted or $C_1$–$C_4$alkyl-substituted $C_5$–$C_{15}$cycloalkenyl; $C_7$–$C_9$phenylalkyl which is unsubstituted or substituted on the phenyl ring by $C_1$–$C_4$alkyl; or tetrahydroabietyl, $R_2$ is $C_1$–$C_{18}$alkylene, $C_2$–$C_{18}$alkylene which is interrupted by oxygen, sulfur or >N—$R_3$; $C_4$–$C_8$alkenylene or phenylethylene, $R_3$ is hydrogen or $C_1$–$C_8$alkyl, m is 0 or 1, and n is a number from 2 to 25, where the group L, the radicals $R_1$, $R_2$ and $R_3$ and the index m are identical or different in the recurring structural units of the formula I.

Alkyl having up to 25 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl; 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl. One of the preferred meanings of $R_1$ and $R_2$ is, for example, $C_1$–$C_{18}$alkyl, in particular $C_1$–$C_{12}$alkyl, for example $C_1$–$C_8$alkyl.

$C_2$–$C_{25}$alkyl which is interrupted by oxygen, sulfur or >N—$R_3$ can be interrupted once or more than once and is, for example, $CH_3$—O—$CH_2$—, $CH_3$—S—$CH_2$—, $CH_3$—NH—$CH_2$—, $CH_3$—N($CH_3$)—$CH_2$—, $CH_3$—O—$CH_2CH_2$—O—$CH_2$—, $CH_3$—(O—$CH_2CH_2$—)$_2$O—$CH_2$—, $CH_3$—(O—$CH_2CH_2$—)$_3$O—$CH_2$— or $CH_3$—(O—$CH_2CH_2$—)$_4$O—$CH_2$—.

Alkenyl having 2 to 24 carbon atoms is a branched or unbranched radical, for example vinyl, propenyl, 2-butenyl, 3-butenyl, isobutenyl, n-2,4-pentadienyl, 3-methyl-2-butenyl, n-2-octenyl, n-2-dodecenyl, isododecenyl, oleyl, n-2-octadecenyl or n-4-octadecenyl. Preference is given to alkenyl having 3 to 18, in particular 3 to 12, carbon atoms.

Unsubstituted or $C_1$–$C_4$alkyl-substituted $C_5$–$C_{15}$cycloalkyl, in particular $C_5$–$C_{12}$cycloalkyl, which preferably contains 1 to 3, in particular 1 or 2, branched or unbranched alkyl radicals, is, for example, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl, cyclooctyl or cyclododecyl. Preference is given to $C_5$–$C_8$cycloalkyl, in particular cyclohexyl.

Unsubstituted or $C_1$–$C_4$alkyl-substituted $C_5$–$C_{15}$cycloalkenyl, which preferably contains 1 to 3, in particular 1 or 2, branched or unbranched alkyl radicals, is, for example, cyclopentenyl, methylcyclopentenyl, dimethylcyclopentenyl, cyclohexenyl, methylcyclohexenyl, dimethylcyclohexenyl, trimethylcyclohexenyl, tert-butylcyclohexenyl, cycloheptenyl, cyclooctenyl or cyclododecenyl. Preference is given to $C_5$–$C_{12}$cycloalkenyl, in particular $C_5$–$C_8$cycloalkenyl, for example cyclohexenyl.

$C_7$–$C_9$phenylalkyl which is unsubstituted or substituted on the phenyl radical by $C_1$–$C_4$alkyl and which preferably contains 1 to 3, in particular 1 or 2, branched or unbranched alkyl radicals is, for example, benzyl, α-methylbenzyl, α,α-dimethylbenzyl, 2-phenylethyl, 2-methylbenzyl, 3-methylbenzyl, 4-methylbenzyl, 2,4-dimethylbenzyl, 2,6-dimethylbenzyl or 4-tert-butylbenzyl. Benzyl is preferred.

$C_1$–$C_{18}$alkylene is a branched or unbranched radical, for example methylene, ethylene, propylene, tetramethylene, pentamethylene, hexamethylene, heptamethylene, octamethylene, decamethylene, dodecamethylene or octadecamethylene. Preference is given to $C_1$–$C_{12}$alkylene, in particular $C_1$–$C_8$alkylene. A preferred meaning of $R_2$ is ethylene or propylene.

$C_2$–$C_{18}$alkylene which is interrupted by oxygen, sulfur or >N—$R_3$ can be interrupted once or more than once and is, for example, —$CH_2$—O—$CH_2$—, —$CH_2$—S—$CH_2$—, —CH$_2$—NH—CH$_2$—, —CH$_2$—N(CH$_3$)—CH$_2$—, —CH$_2$—O—CH$_2$CH$_2$—O—CH$_2$—, —CH$_2$—(O—CH$_2$CH$_2$—)$_2$O—CH$_2$—, —CH$_2$—(O—CH$_2$CH$_2$—)$_3$O—CH$_2$—, —CH$_2$—(O—CH$_2$CH$_2$—)$_4$O—CH$_2$— or —CH$_2$CH$_2$—S—CH$_2$CH$_2$—.

C$_4$–C$_8$alkenylene R$_2$ is, for example, 2-buten-1,4-ylene.

The group L, the radicals R$_1$, R$_2$ and R$_3$ and the index m are preferably identical in the recurring structural units of the formula I.

Preference is given to the oligomeric compounds of the formula I in which

R$_1$ is C$_1$–C$_{18}$alkyl, C$_2$–C$_{18}$alkyl which is interrupted by oxygen, sulfur or >N—R$_3$; C$_3$–C$_{18}$alkenyl, unsubstituted or C$_1$–C$_4$alkyl-substituted C$_5$–C$_{12}$cycloalkyl; unsubstituted or C$_1$–C$_4$alkyl-substituted C$_5$–C$_{12}$cycloalkenyl; C$_7$–C$_9$phenylalkyl which is unsubstituted or substituted on the phenyl ring by C$_1$–C$_4$alkyl; or tetrahydroabietyl.

Preference is also given to the oligomeric compounds of the formula I in which R$_2$ is C$_1$–C$_{12}$alkylene, C$_2$–C$_{12}$alkylene which is interrupted by oxygen; C$_4$–C$_8$alkenylene or phenylethylene.

Likewise preferred are the oligomeric compounds of the formula I in which R$_2$ is ethylene or propylene.

Particular preference is given to the oligomeric compounds of the formula I in which R$_1$ is C$_1$–C$_{12}$alkyl, C$_2$–C$_{12}$alkyl which is interrupted by oxygen; C$_3$–C$_{12}$alkenyl, C$_5$–C$_8$cycloalkyl, C$_5$–C$_8$cycloalkenyl, C$_7$–C$_9$phenylalkyl or tetrahydroabietyl, R$_2$ is C$_1$–C$_8$alkylene or phenylethylene, and n is a number from 2 to 15.

Of particular interest are the oligomeric compounds of the formula I in which

R$_1$ is C$_1$–C$_{12}$alkyl, C$_3$–C$_{12}$alkenyl, cyclohexyl, benzyl or tetrahydroabietyl, R$_2$ is ethylene, propylene or phenylethylene, and n is a number from 2 to 15.

Of specific interest are the oligomeric compounds of the formula I in which

R$_1$ is C$_1$–C$_8$alkyl, cyclohexyl or tetrahydroabietyl,

R$_2$ is ethylene, and n is a number from 2 to 10.

The novel oligomeric compounds of the formula I can be prepared in a manner known per se.

The invention furthermore relates to a preferred process for the preparation of oligomeric compounds of the formula I, which comprises reacting a compound of the formula II or a mixture of compounds of the formula II

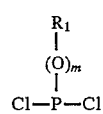
(II)

in which m and R$_1$ are as defined above, with a compound of the formula III or a mixture of compounds of the formula III

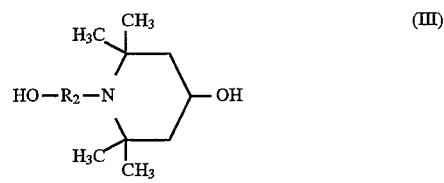
(III)

in which R$_2$ is as defined above.

The reaction is carried out in the melt or in the presence of a suitable organic, polar or apolar, aprotic solvent. This reaction is preferably carried out in the presence of a base at temperatures between −20° C. and the boring point of the solvent, in particular at temperatures between 20° and 150° C.

Bases such as mines can simultaneously also be used as solvent.

The base can be employed in various mounts, from catalytic via stoichiometric amounts up to an excess of several times the molar amount with respect to the compounds of the formula II or compounds of the fomula III employed. The hydrogen chloride formed during the reaction is, if appropriate, converted through the base into chloride, which can be removed by filtration and/or washing with a suitable aqueous or solid phase; a second, water-immiscible solvent can also be employed here. The products are expediently isolated by evaporating the organic phase and drying the residue.

Suitable solvents for carrying out the reaction include hydrocarbons (for example mesitylene, toluene, xylene, hexane, pentane or other petroleum ether fractions), halogenated hydrocarbons (for example di- or trichloromethane, 1,2-dichloroethane, 1,1,1-trichloroethane or chlorobenzene), ethers (for example diethyl ether, dibutyl ether or tetrahydrofuran), ketones (for example acetone, ethyl methyl ketone, diethyl ketone, methyl propyl ketone or cyclohexanone), furthermore acetonitrile, butyl acetate, dimethyl formamide, dimethyl sulfoxide or N-methylpyrrolidone.

Suitable bases include primary, secondary and in particular tertiary amines (for example trimethylamine, triethylamine, tributylamine, N,N-dimethylaniline, N,N-diethylaniline or pyridine), hydrides (for example lithium hydride, sodium hydride or potassium hydride) or alkoxides (for example sodium methoxide).

If hydrides (for example sodium hydride, sodium borohydride or lithium aluminium hydride), alkali metals, alkali metal hydroxides or sodium methoxide are used as bases, the corresponding alkoxide of the compound of the formula III can first be formed; any reaction product formed (for example water or methanol) is removed by distillation (for example as an azeotrope with toluene) before the reaction with the compound of the formula II.

The structural composition of the oligomeric compounds of the formula I depends on the reaction conditions, for example the solvent or the reaction temperature, and the molar mixing ratio and the concentration of the compounds of the formulae II and III.

Both the compound of the formula II and the compound of the formula III can be used in a molar excess. However, it is preferred to use the HALS-diol of the formula III in excess. Preferred molar mixing ratios between the compounds of the formulae II and III are from 1.9:1 to 1:1.9, particularly preferably 1.05:1 to 1:1.8, in particular from 1:1.3 to 1:1.8.

The present invention therefore also relates to oligomeric products obtainable by reacting a compound of the formula II or a mixture of compounds of the formula II with a compound of the formula III or a mixture of compounds of the formula III.

The preparation of the compounds of the formulae II and III is known.

The compounds of the formula II in which m=1 are known or can be prepared by processes known per se, as described, for example, in DE-A-3 928 291 or by R. A. Bartlett et al, J. Amer. Chem. Soc. 109 (19), 5699 (1987).

The compounds of the formula II in which m=0 are likewise known or can be prepared by processes known per se, as described, for example, in Org. Syntheses Coll. Vol. IV, 784 (1963) and by T. Weil et el., Helv. Chim. Acta 1952, 1412, and F. Nief et al., Tetrahedron 47 (33), 6673 (1991).

The compounds of the formula II required for the preparation of the novel compounds of the formula I can be prepared in situ analogously to the abovementioned literature procedures, and reacted further, without isolation, with a compound of the formula III to give the compounds of the formula I.

The HALS compounds of the formula III are known or can be prepared by processes known per se, as described, for example, in U.S. Pat. No. 4,233,412.

L can have identical or different meanings in the recurring structural units of the formula I.

If the HALS compound of the formula III is used in excess, the terminal groups of the oligomeric compounds of the formula I are, as shown in the formula IV

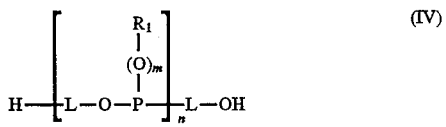
(IV)

predominantly hydroxyl groups, which, if desired, can easily be derivatized by known methods. For example, these hydroxyl groups can be esterified by means of acid halides, for example carboxylic acid halides or phosphoric acid halides, or acid anhydrides; silylated using silyl halides; alkylated or benzylated using alkyl or benzyl halides; reacted with isocyanates to give the urethanes; reacted with isothiocyanates to give the thiourethanes; reacted with sulfonyl halides and, for example, thionyl chloride to give the halides; or reacted with chlorophosphites, for example of the formula V, VI or VII

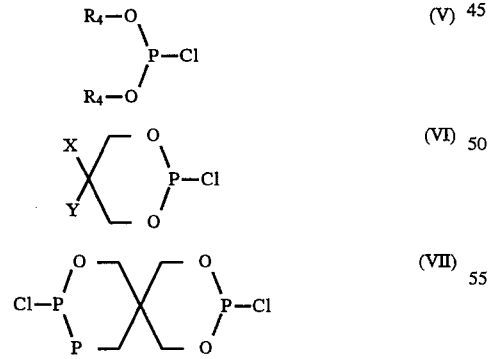
(V)
(VI)
(VII)

in which $R_4$ is, for example, $C_1$–$C_{25}$alkyl, unsubstituted or $C_1$–$C_4$alkyl-substituted phenyl; or $C_7$–$C_9$phenylalkyl, and X and Y, independently of one another, are hydrogen or $C_1$–$C_4$alkyl or, together with the carbon atom to which they are bonded, form a 3,4-dehydrocyclohexylidene ring.

$C_1$–$C_4$alkyl-substituted phenyl, which preferably contains 1 to 3, in particular 1 or 2, alkyl groups, is, for example, o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

If the compound of the formula II is used in excess, the terminal groups of the oligomeric compounds of the formula I in some cases also carry reactive

groups, as shown in the formulae VIII, IX and X

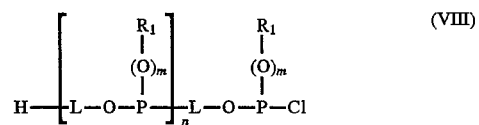
(VIII)

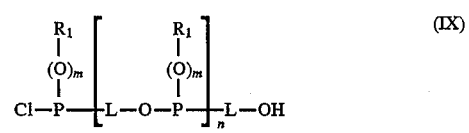
(IX)

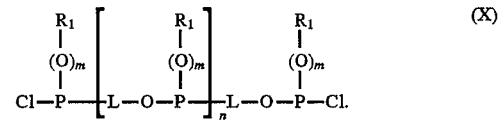
(X)

The chlorine atoms can be substituted by additional nucleophiles, for example phenols, alcohols, amines, mercaptans or dialkyl phosphites, by known methods with elimination of hydrochloric acid. Suitable alcohols are $C_1$–$C_8$alkanols, for example methanol, ethanol, n-propanol or n-butanol.

The oligomeric compounds of the formula I can also be in the form of ring systems of the formula XI

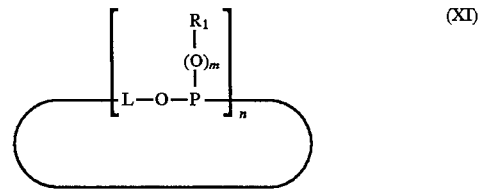
(XI)

in which the hydroxyl terminal group in L cyclizes with the other chain end

with elimination of hydrochloric acid.

The present invention preferably relates to oligomeric compounds of the formula XII

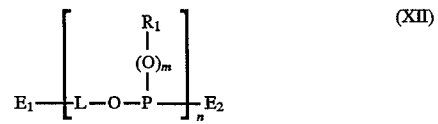
(XII)

in which the terminal group $E_1$ is hydrogen,

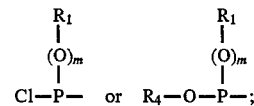

the terminal group $E_2$ is a radical of the formula —L—OH,

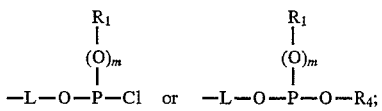

or furthermore the terminal groups $E_1$ and $E_2$ together form a direct bond (cyclic compounds); and $R_4$ is $C_1$-$C_8$alkyl.

Particular preference is given to oligomeric compounds of the formula XII in which the terminal group $E_1$ is hydrogen and the terminal group $E_2$ is a radical of the formula —L—OH, in which L is as defined above.

The novel compounds of the formula I are suitable for the stabilization of organic materials against oxidative, thermal or light-induced degradation.

Examples of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, mines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidenenorbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The invention therefore furthermore relates to compositions comprising (a) an organic material subjected to oxidative, thermal or light-induced degradation and (b) at least one oligomeric compound of the formula I or at least one oligomeric product obtainable by reacting a compound of the formula II or a mixture of compounds of the formula II with a compound of the formula III or a mixture of compounds of the formula III.

The organic materials to be protected are preferably natural, semisynthetic or preferably synthetic organic materials. Particular preference is given to thermoplastic polymers, in particular PVC or polyolefins, in particular polyethylene and polypropylene.

Particular emphasis should be placed on the action of the novel compounds against thermal and oxidative degradation, in particular on heating, as occurs in the processing of thermoplastics. The novel compounds are therefore highly suitable for use as processing stabilizers.

The oligomeric compounds of the formula I are preferably added to the material to be stabilized in amounts of from 0.01 to 10%, for example from 0.01 to 5%, preferably from 0.025 to 3%, in particular from 0.025 to 1%, based on the weight of the organic material to be stabilized.

In addition to the oligomeric compounds of the formula I, the novel compositions can contain further costabilizers, for example the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tertbutylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl) disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylene-bis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl) dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-i,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphortic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl- 1-phospha-2,6,7-trioxabicyclo[2.2.2]octane.

1.17. Amides of β-(3,5-di-tert-butyl-4-hydroxyphenyl) propionic acid e.g. N,N'-bis(3,5-ditert-butyl-4-hydroxyphenylpropionyl)hexamethylenediamine, N,N'-bis(3,5-di-tert-butyl-4-hydroxyphenylpropionyl) trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazol, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tertbutyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$)$_3$-]$_2$, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis (4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetra-methylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1, 2,3,4-butane-tetracarboxylate, 1,1'-(1,2-ethanediyl)bis(3,3, 5,5-tetramethylpiperazinone), 4-benzoyl-2,2,6,6-tetramethylpiperidine, 4-stearyloxy-2,2,6,6-tetramethylpiperidine, bis(1,2,2,6,6-penta-methylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decan-2, 4-dion, bis(1-octyloxy-2,2,6,6-tetramethylpiperidyl) sebacate, bis(1-octyloxy-2,2,6,6-tetramethylpiperidyl) succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis (4-n-butyl-amino- 2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2, 5-dione, 3-dodecyl-1-(1,2,2,6,6-pentamethyl-4-piperidyl) pyrrolidine-2,5-dione.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8.2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1, 3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl)hydrazine, 3-salicyloylamino-1,2, 4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4, 6-tris(tert-butylphenyl)pentaerythritol diphsophite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1, 3,2-dioxaphosphocin, bis(2,4-di-tert-butyl-6-methylphenyl) methylphosphite, bis(2,4-di-tert-butyl-6-methylphenyl) ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, area derivatives, hydrazine derivatives, amines, polyamides, polyarethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticisers, lubricants, emulsifiers, pigments, optical brighteners, flameproofing agents, antistatic agents and blowing agents.

11. Benzofuranones and indolinones, for example those disclosed in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4 316 611, DB-A-4 316 622, DE-A-4 316 876, EP-A-0 589 839 or EP-A-0 591 102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]-phenyl)benzofuran-2-one], 5,7-di-tert-butyl-3-(4-ethoxyphenyl)benzofuran-2-one, 3-(4-acetoxy- 3,5-dimethylphenyl)-5,7-di-tert-butyl-benzofuran-2-one, 3-(3,5-dimethyl-4-pivaloyloxyphenyl)-5, 7-di-tert-butyl-benzofuran-2-one.

The costabilizers, with the exception of the benzofuranones mentioned under point 11, are added, for example, in concentrations of from 0.01 to 10%, based on the total weight of the material to be stabilized.

Other preferred compositions comprise, in addition to component (a) and the oligomeric compounds of the formula I, other additives, in particular phenolic antioxidants, light stabilizers and/or processing stabilizers.

Particularly preferred additives are phenolic antioxidants (point 1 in the list), sterically hindered amines (point 2.6 in the list), phosphites and phosphonites (point 4 in the list) and peroxide scavengers (point 5 in the list).

Other additives (stabilizers) which are likewise particularly preferred are benzofuran-2-ones, as described, for example, in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4 316 611, DE-A-4 316 622, DE-A-4 316 876, EP-A-0 589 839 and EP-A-0 591 102.

Examples of such benzofuran-2-ones are compounds of the formula

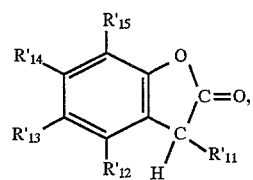

in which $R'_{11}$ is an unsubstituted or substituted carbocyclic or heterocyclic aromatic ring system;

$R'_{12}$ is hydrogen;

$R'_{14}$ is hydrogen, alkyl having 1 to 12 carbon atoms, cyclopentyl, cyclohexyl or chlorine;

$R'_{13}$ is as defined for $R'_{12}$ or $R'_{14}$ or is a radical of the formula

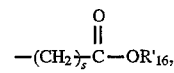

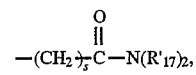

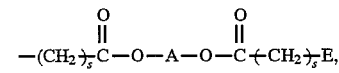

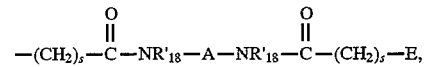

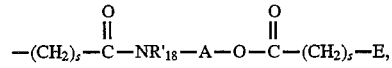

or —D—E, in which $R'_{16}$ is hydrogen, alkyl having 1 to 18 carbon atoms, alkyl having 2 to 18 carbon atoms which is interrupted by oxygen or sulfur, dialkylaminoalkyl having a total of 3 to 16 carbon atoms, cyclopentyl, cyclohexyl, phenyl or phenyl which is substituted by 1 to 3 alkyl radicals having a total of at most 18 carbon atoms;

s is 0, 1 or 2;

the substituents $R'_{17}$, independently of one another, are hydrogen, alkyl having 1 to 18 carbon atoms, cyclopentyl, cyclohexyl, phenyl, phenyl which is substituted by 1 or 2 alkyl radicals having a total of at most 16 carbon atoms, a radical of the formula —$C_2H_4OH$, —$C_2H_4$—O—$C_tH_{2t+1}$ or

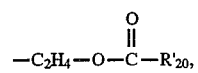

or, together with the nitrogen atom to which they are bonded, form a piperidine or morpholine radical;

t is from 1 to 18;

$R'_{20}$ is hydrogen, alkyl having 1 to 22 carbon atoms or cycloalkyl having 5 to 12 carbon atoms;

A is alkylene having 2 to 22 carbon atoms which may be interrupted by nitrogen, oxygen or sulfur;

$R'_{18}$ is hydrogen, alkyl having 1 to 18 carbon atoms, cyclopentyl, cyclohexyl, phenyl, phenyl which is substituted by 1 or 2 alkyl radicals having a total of at most 16 carbon atoms, or benzyl;

$R'_{19}$ is alkyl having 1 to 18 carbon atoms;

D is —O—, —S—, —SO—, —SO$_2$— or —C(R'$_{21}$)$_2$—;

the substituents $R'_{21}$, independently of one another, are hydrogen, $C_1$-$C_{16}$alkyl, where the two $R'_{21}$ radicals together contain 1 to 16 carbon atoms, $R'_{21}$ is furthermore phenyl or a radical of the formula

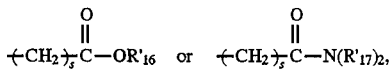

in which s, $R'_{16}$ and $R'_{17}$ are as defined above;

E is a radical of the formula

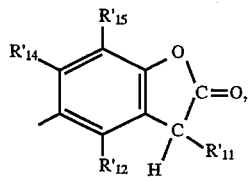

in which $R'_{11}$, $R'_{12}$ and $R'_{14}$ are as defined above; and $R'_{15}$ is hydrogen, alkyl having 1 to 20 carbon atoms, cyclopentyl, cyclohexyl, chlorine or a radical of the formula

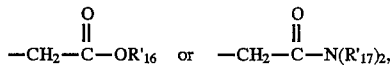

in which $R'_{16}$ and $R'_{17}$ are as defined above, or $R'_{15}$ is together with $R'_{14}$ forms a tetramethylene radical.

Preference is given to benzofuran-2-ones in which $R'_{13}$ is hydrogen, alkyl having 1 to 12 carbon atoms, cyclopentyl, cyclohexyl, chlorine or a radical of the formula

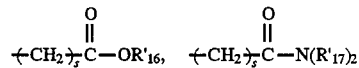

or —D—E, in which s, $R'_{16}$, $R'_{17}$, D and E are as defined above, and $R'_{16}$ is, in particular, hydrogen, alkyl having 1 to 18 carbon atoms, cyclopentyl or cyclohexyl.

Preference is also given to benzofuran-2-ones in which $R'_{11}$ is phenyl or phenyl which is substituted by 1 or 2 alkyl radicals having a total of at most 12 carbon atoms;

$R'_{12}$ is hydrogen;

$R'_{14}$ is hydrogen or alkyl having 1 to 12 carbon atoms;

$R'_{13}$ is hydrogen, alkyl having 1 to 12 carbon atoms,

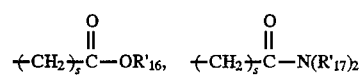

or —D—E;

$R'_{15}$ is hydrogen, alkyl having 1 to 20 carbon atoms,

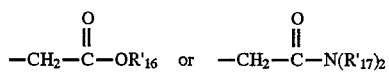

or $R'_{15}$ together with $R'_{14}$ forms a tetramethylene radical, where s, $R'_{16}$, $R'_{17}$, D and E are as defined at the outset.

Likewise of particular interest are benzofuran-2-ones in which $R'_{13}$ is hydrogen, alkyl having 1 to 12 carbon atoms or —D—E; $R'_{12}$ and $R'_{14}$, independently of one another, are hydrogen or alkyl having 1 to 4 carbon atoms; and $R'_{15}$ is alkyl having 1 to 20 carbon atoms, where D and E are as defined at the outset.

Finally, likewise of particular interest are benzofuran-2-ones in which $R'_{13}$ is alkyl having 1 to 4 carbon atoms or —D—E; $R'_{12}$ and $R'_{14}$ are hydrogen; and $R'_{15}$ is alkyl having 1 to 4 carbon atoms, cyclopentyl or cyclohexyl, where D is a —C(R'$_{21}$)$_2$— group and E is a radical of the formula

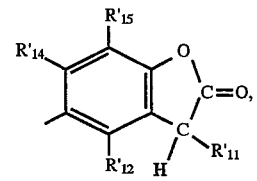

where the substituents $R'_{21}$ are identical or different and are each alkyl having 1 to 4 carbon atoms, and $R'_{11}$, $R'_{12}$, $R'_{14}$ and $R'_{15}$ are as defined above.

The amount of benzofuran-2-ones additionally employed can vary within broad limits. For example, they can be present in the novel compositions in amounts of from 0.0001 to 5% by weight, preferably from 0.001 to 2% by weight, in particular from 0.01 to 2% by weight.

The oligomeric compounds of the formula I and any further additives are incorporated into the polymeric, organic material by known methods, for example before or during shaping or alternatively by application of the dissolved or dispersed compounds to the polymeric, organic material, if necessary with subsequent evaporation of the solvent. The oligomeric compounds of the formula I can also be added to the materials to be stabilized in the form of a masterbatch, which contains these in, for example, a concentration from 2.5 to 25% by weight.

The oligomeric compounds of the formula I can also be added before or during polymerization or before crosslinking.

The oligomeric compounds of the formula I can be incorporated into the material to be stabilized in pure form or encapsulated in waxes, oils or polymers.

The oligomeric compounds of the formula I can also be sprayed onto the polymer to be stabilized. They are capable of diluting other additives (for example the conventional additives mentioned above) or their melts, so that they can also be sprayed onto the polymer to be stabilized together with these additives. A particularly advantageous method is the addition by spraying during deactivation of the polymerization catalysts, where, for example, the steam used for deactivation can be used for the spraying.

In the case of polyolefins polymerized in bead form, it may, for example, be advantageous to apply the oligomeric compounds of the formula I, if desired together with other additives, by spraying.

The materials stabilized in this way can be used in a very wide variety of forms, for example as films, fibres, tapes, moulding compositions, profiles or as binders for paints, adhesives or adhesive cements.

As mentioned above, the organic materials to be protected are preferably organic polymers, particularly synthetic polymers. Thermoplastic materials, in particular polyolefins, are particularly advantageously protected. In particular, the excellent effectiveness of the oligomeric compounds of the formula I as processing stabilizers (heat stabilizers) should be emphasized. For this purpose, they are advantageously added to the polymer before or during processing thereof. However, other polymers (for example elastomers) or lubricants or hydraulic fluids can also be stabilized against degradation, for example light-induced or thermo-oxidative degradation. Elastomers are given in the above list of possible organic materials.

Suitable lubricants and hydraulic fluids are based, for example, on mineral or synthetic oils or mixtures thereof. The lubricants are known to the person skilled in the art and are described in the relevant specialist literature, for example in Dieter Klamann, "Schmierstoffe und verwandte Produkte" [Lubricants and Related Products] (Verlag Chemic, Weinheim, 1982), in Schewe-Kobek, "Das Schmiermittel-Taschenbuch" [The Lubricant Handbook] (Dr. Alfred Hüthig-Verlag, Heidelberg, 1974) and in "Ullmanns Enzykopädie der technischen Chemic" [Ullmann's Encyclopedia of Industrial Chemistry], Vol. 13, pages 85–94 (Verlag Chemie, Weinheim, 1977).

A preferred embodiment of the present invention is therefore the use of oligomeric compounds of the formula I and products obtainable by reacting a compound of the formula II or a mixture of compounds of the formula II with a compound of the formula III or a mixture of compounds of the formula III, for the stabilization of organic materials against oxidative, thermal or light-induced degradation.

The novel oligomeric compounds of the formula I are distinguished by pronounced excellent hydrolysis stability and advantageous colouring behaviour, ie low discoloration of the organic materials during processing.

Organic materials which have been stabilized by means of the compounds of the present invention are particularly well protected against light-induced degradation.

The present invention therefore also relates to a process for the stabilization of an organic material against oxidative, thermal or light-induced degradation, which comprises incorporating or applying at least one oligomeric compound of the formula I or at least a product obtainable by reacting a compound of the formula II or a mixture of compounds of the formula II with a compound of the formula III or a mixture of compounds of the formula III, into or to this material.

The examples below illustrate the invention in greater detail. Parts and percentages are by weight.

EXAMPLE 1

Preparation of the Oligomeric Compound (101)
(Table 1)

a) A solution of 4.41 g (50.0 mmol) of 2,2-dimethyl-1-propanol (neopentyl alcohol in 10 ml of dichloromethane is added dropwise over the course of 20 minutes at room temperature to a stirred solution, under a nitrogen atmosphere, of 8.93 g (65.0 mmol) of phosphorus trichloride in 40 ml of dichloromethane. The hydrochloric acid gas formed during the reaction is neutralized by being passed into dilute sodium hydroxide solution. The reaction mixture is subsequently refluxed for 2 hours. The dichloromethane and the excess phosphorus trichloride are removed by distillation on a vacuum rotary evaporator. The residue yields 8.51 g (90%) of neopentyl phosphorodichloridite, which is used without further purification for the next step (Example 1b).

b) 8.51 g (45 mmol, 1.0 equivalent) of neopentyl phosphorodichloridite (Example 1a) is added dropwise at room temperature to a stirred suspension, under a nitrogen atmosphere, of 15.40 g (77.0 mmol, 1.7 equivalents) of N-2'-hydroxyethyl-4-hydroxy-2,2,6,6-tetramethylpiperidine and 11.38 g (113 mmol, 2.5 equivalents) of triethylamine in 200 ml of toluene. The reaction mixture is subsequently stirred vigorously for 5 hours at 95° C. After cooling to room temperature, the white suspension is filtered through Celite, and the filtrate is evaporated on a vacuum rotary evaporator. Drying of the residue in a high vacuum gives 8.0 g (56%) of the oligomeric compound (101) (Table 1) as a viscous oil.

The weight average molecular weight Mw and the number average molecular weight Mn are determined by gel permeation chromatography (GPC).

Analogously to Example 1, 9.05 g (45.0 mmol) of cyclohexyl phosphorodichloridite and 15.4 g (77.0 mmol) of N-2'-hydroxyethyl-4-hydroxy-2,2,6,6-tetramethylpiperidine are reacted to give 5.85 g (40%) of the oligomeric compound (102) (Table 1) as a viscous oil.

EXAMPLE 2

Preparation of the Oligomeric Compound (103)
(Table 1)

A solution of 6.64 g (22.0 mmol, 1.0 equivalent) of tetrahydroabietyl dichlorophosphite [EP-A-0 487 036, Examples 1, 2 and 4) in 10 ml of toluene is added dropwise at room temperature to a stirred solution, under a nitrogen atmosphere, of 6.64 g (33.0 mmol, 1.5 equivalents) of N-2'-hydroxyethyl-4-hydroxy-2,2,6,6-tetramethylpiperidine and 5.34 g (53.0 mmol, 2.4 equivalents) of triethylamine in 30 ml of toluene. The reaction mixture is subsequently stirred at a temperature of 95° C. for 10 hours. The white suspension is filtered through Celite, and the filtrate is evaporated on a vacuum rotary evaporator. Drying of the residue in a high vacuum gives 4.5 g (33%) of the oligomeric compound (103) (Table 1), m.p. 245° C.

EXAMPLE 3

Preparation of the Oligomeric Compound (104)
(Table 1)

4 ml (4.56 g, 21.2 mmol, 1.0 equivalent) of dichlorooctyl phosphine is added dropwise at room temperature to a stirred solution, under a nitrogen atmosphere, of 7.25 g (36.0 mmol, 1.7 equivalents) of N-2'-hydroxyethyl-4-hydroxy-2, 2,6,6-tetramethylpiperidine and 5.34 g (53.0 mmol, 2.5 equivalents) of triethylamine in 100 ml of toluene. The reaction mixture is subsequently stirred for 3 hours at a temperature of 95° C. The white suspension is filtered through Celite, and the filtrate is evaporated on a vacuum rotary evaporator. Drying of the residue in a high vacuum gives 6.9 g (68%) of the oligomeric compound (104) (Table 1) as a colourless oil.

TABLE 1

| No. | Compound | $R_2$ in L | Mn | Mw/Mn | m.p. (°C.) | % P |
|-----|----------|-----------|-----|-------|------------|-----|
| 101 | [L—O—P(O—CH$_2$—C(CH$_3$)$_3$)]$_n$ (neopentyl group: H$_3$C—C(CH$_3$)(CH$_3$)—CH$_2$—O—) | —CH$_2$CH$_2$— | 866 | 2.11 | Oil | 7.59 |
| 102 | [L—O—P(O—cyclohexyl)]$_n$ | —CH$_2$CH$_2$— | 1087 | 2.56 | Oil | 7.84 |
| 103 | [L—O—P(O—dehydroabietyl)]$_n$ (with CH$_3$, CH(CH$_3$)$_2$, CH$_3$, H, CH$_3$ substituents on decalin system) | —CH$_2$CH$_2$— | 1499 | 2.3 | 245 | 5.7 |
| 104 | [L—O—P(O—CH$_2$(CH$_2$)$_6$CH$_3$)]$_n$ | —CH$_2$CH$_2$— | 705 | 1.4 | Oil | 8.11 |

EXAMPLE 4

Stabilization of Polypropylene During Multiple Extrusion 1.3 kg of polypropylene powder (®Profax 6501) which has been prestabilized by means of 0.025% of Irganox® 1076 (n-octadecyl 3-[3,5-di-tert-butyl-4-hydroxyphenyl] propionate) (having a melt flow index of 3.2, measured at 230° C. and 2.16 kg) are mixed with 0.05% of Irganox® 1010 (pentaerythrityl tetrakis[3-(3,5-di-tert-butyl-4-hydroxyphenyl)propionate]), 0.05% of calcium stearate, 0.03% of dihydrotalcite [DHT 4A®, Kyowa Chemical Industry Co., Ltd., Mg$_{4.5}$Al$_2$(OH)$_{13}$CO$_3$•3.5 H$_2$O] and 0.05% of the compound from Table 1. This mixture is extruded in an extruder having a barrel diameter of 20 mm and a length of 400 mm at 100 revolutions per minute, the three heating zones being set at the following temperatures: 260°, 270°, 280° C. The extrudate is cooled by drawing through a water bath and subsequently granulated. These granules are re-extruded. After 3 extrusions, the melt flow index is measured (at 230° C. and 2.16 kg). A large increase in the melt flow index means considerable chain degradation, ie poor stabilization. The results are shown in Table 2.

TABLE 2

| Compound from Table 1 | Melt flow index after 3 extrusions |
|---|---|
| — | 20.0 |
| 101 | 6.1 |
| 102 | 4.9 |

EXAMPLE 5

Stabilization of Polyethylene During Processing 100 parts of polyethylene powder (Lupolen® 5260 Z) are mixed with 0.05 part of Irganox® 1010 (pentaerythrityl tetrakis[3-(3,5-di-tert-butyl-4-hydroxyphenyl)propionate]) and 0.1 part of stabilizer from Table 1, and the mixture is compounded in a Brabender Plastograph at 220° C. and 50 revolutions per minute. During this time, the compounding resistance is recorded continuously as torque. During the compound time, the polymer, after an extended constant time, begins to crosslink, which is evident from the rapid increase in torque. Table 3 shows the time before significant increase in the torque as a measure of the stabilizer action. The longer this time, the better the stabilizer action.

TABLE 3

| Compound from Table 1 | Time before torque increase (min.) |
| --- | --- |
| — | 5.0 |
| 101 | 15.0 |
| 102 | 13.5 |
| 104 | 14.0 |

What is claimed is:

1. An oligomeric compound containing a structural unit of the formula I

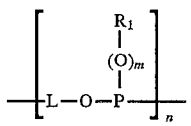  (I)

in which L is a group of the formula

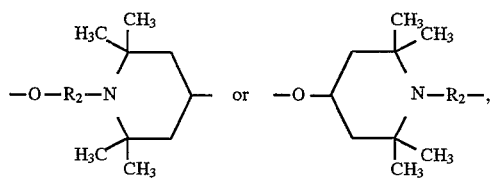

where the oxygen in the group L is in each case bonded to the phosphorus in the recurring structural unit and the radical $R_2$ or the carbon in the 4-position of the piperidinyl ring in the group L is in each case bonded to the oxygen in the recurring structural unit;

$R_1$ is $C_1$–$C_{25}$alkyl, $C_2$–$C_{25}$alkyl which is interrupted by oxygen, sulfur or >N—$R_3$; $C_2$–$C_{24}$alkenyl, unsubstituted or $C_1$–$C_4$alkyl-substituted $C_5$–$C_{15}$cycloalkyl; unsubstituted or $C_1$–$C_4$alkyl-substituted $C_5$–$C_{15}$cycloalkenyl; $C_7$–$C_9$phenyl alkyl which is unsubstituted or substituted on the phenyl ring by $C_1$–$C_4$alkyl; or tetrahydroabietyl, $R_2$ is $C_1$–$C_{18}$alkylene, $C_2$–$C_{18}$alkylene which is interrupted by oxygen, sulfur or >N—$R_3$; $C_4$–$C_8$alkenylene or phenylethylene, $R_3$ is hydrogen or $C_1$–$C_8$alkyl, m is 0 or 1, and n is a number from 2 to 25, where the group L, the radicals $R_1$, $R_2$ and $R_3$ and the index m are identical or different in the recurring structural units of the formula I.

2. An oligomeric compound according to claim 1, in which $R_1$ is $C_1$–$C_{18}$alkyl, $C_2$–$C_{18}$alkyl which is interrupted by oxygen, sulfur or >N—$R_3$; $C_3$–$C_{18}$alkenyl, unsubstituted or $C_1$–$C_4$alkyl-substituted $C_5$–$C_{12}$cycloalkyl; unsubstituted or $C_1$–$C_4$alkyl-substituted $C_5$–$C_{12}$cycloalkenyl; $C_7$–$C_9$phenylalkyl which is unsubstituted or substituted on the phenyl ring by $C_1$–$C_4$alkyl; or tetrahydroabietyl.

3. An oligomeric compound according to claim 1, in which $R_2$ is $C_1$–$C_{12}$alkylene, $C_2$–$C_{12}$alkylene which is interrupted by oxygen; $C_4$–$C_8$alkenylene or phenylethylene.

4. An oligomeric compound according to claim 1, in which $R_2$ is ethylene or propylene.

5. An oligomeric compound according to claim 1, in which $R_1$ is $C_1$–$C_{12}$alkyl, $C_2$–$C_{12}$alkyl which is interrupted by oxygen; $C_3$–$C_{12}$alkenyl, $C_5$–$C_8$cycloalkyl, $C_5$–$C_8$cycloalkenyl, $C_7$–$C_9$phenylalkyl or tetrahydroabietyl, $R_2$ is $C_1$–$C_8$alkylene or phenylethylene, and n is a number from 2 to 15.

6. An oligomeric compound according to claim 1, in which $R_1$ is $C_1$–$C_{12}$alkyl, $C_3$–$C_{12}$alkenyl, cyclohexyl, benzyl or tetrahydroabietyl, $R_2$ is ethylene, propylene or phenylethylene, and n is a number from 2 to 15.

7. An oligomeric compound according to claim 1, in which $R_1$ is $C_1$–$C_8$alkyl, cyclohexyl or tetrahydroabietyl, $R_2$ is ethylene, and n is a number from 2 to 10.

8. A process for the preparation of an oligomeric compound of the formula I according to claim 1, which comprises reacting a compound of the formula II or a mixture of compounds of the formula II

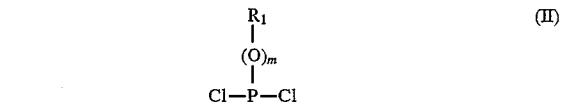  (II)

in which m and $R_1$ are as defined in claim 1, with a compound of the formula III or a mixture of compounds of the formula III

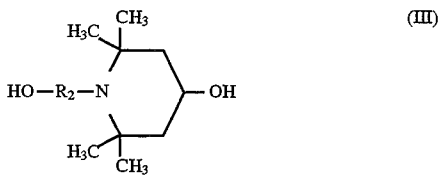  (III)

in which $R_2$ is as defined in claim 1.

9. An oligomeric product obtained by reacting a compound of the formula II or a mixture of compounds of the formula II with a compound of the formula III or a mixture of compounds of the formula III

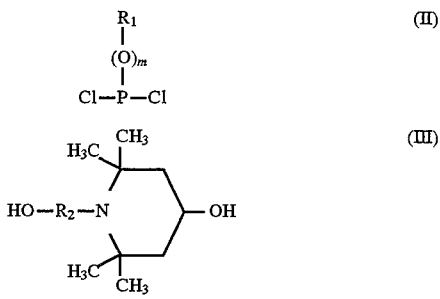

in which $R_1$ is $C_1$–$C_{25}$alkyl, $C_2$–$C_{25}$alkyl which is interrupted by oxygen, sulfur or >N—$R_2$; $C_2$–$C_{24}$alkenyl, unsubstituted or $C_1$–$C_4$alkyl-substituted $C_5$–$C_{15}$cycloalkyl; unsubstituted or $C_1$–$C_4$alkyl-substituted $C_5$–$C_{15}$cycloalkenyl; $C_7$–$C_9$phenylalkyl which is unsubstituted or substituted on the phenyl ring by $C_1$–$C_4$alkyl; or tetrahydroabietyl, $R_2$ is $C_2$–$C_{18}$alkylene, $C_2$–$C_{18}$alkylene which is interrupted by oxygen, sulfur or >N—$R_3$; $C_4$–$C_8$alkenylene or phenylethylene, $R_3$ is hydrogen or $C_1$–$C_8$alkyl, and m is 0 or 1.

10. A composition comprising a) an organic material which is subjected to oxidative, thermal or light-induced degradation; and b) at least one oligomeric compound of the formula I according to claim 1.

11. A composition comprising a) an organic material which is subjected to oxidative, thermal or light-induced degradation; and b) at least one oligomeric product according to claim 9.

12. A composition according to claim 10, additionally comprising further additives in addition to components (a) and (b).

13. A composition according to claim 12, wherein the further additives are phenolic antioxidants, light stabilizers and/or processing stabilizers.

14. A composition according to claim 12 wherein the further additive is at least one compound of the benzofuran-2-one type.

15. A composition according to claim 10, wherein component (a) is a natural, semisynthetic or synthetic polymer.

16. A composition according to claim 10, wherein component (a) is a thermoplastic polymer.

17. A composition according to claim 10, wherein component (a) is a polyolefin.

18. A composition according to claim 10, wherein component (a) is polyethylene or polypropylene.

19. A process for the stabilization of an organic material against oxidative, thermal or light-induced degradation, which process comprises incorporating in, or applying to, said organic material at least one compound of the formula I according to claim 1.

20. A process for the stabilization of an organic material against oxidative, thermal or light-induced degradation, which process comprises incorporating into, or applying to, said organic material at least one oligomeric product according to claim 9.

21. A composition according to claim 11 additionally comprising further additives in addition to components (a) and (b).

22. A composition according to claim 21, wherein the further additives are phenolic antioxidants, light stabilizers and/or processing stabilizers.

23. A composition according to claim 21, wherein the further additive is at least one compound of the benzofuran-2-one type.

24. A composition according to claim 11, wherein component (a) is a natural, semisynthetic or synthetic polymer.

25. A composition according to claim 11, wherein component (a) is a thermoplastic polymer.

26. A composition according to claim 11, wherein component (a) is a polyolefin.

27. A composition according to claim 11, wherein component (a) is polyethylene or polypropylene.

* * * * *